United States Patent [19]

Lass

[11] Patent Number: 4,565,201

[45] Date of Patent: Jan. 21, 1986

[54] SIGNAL PROCESSING APPARATUS AND HIGH RESOLUTION ELECTROCARDIOGRAPH EQUIPMENT INCLUDING SAME

[75] Inventor: Yoram Lass, Tel Aviv, Israel

[73] Assignee: Fidelity Medical (Israel) Ltd., Tel Aviv, Israel

[21] Appl. No.: 463,480

[22] Filed: Feb. 3, 1983

[30] Foreign Application Priority Data

Jan. 11, 1983 [IL] Israel .................................. 67660

[51] Int. Cl.[4] .............................................. A61B 5/04
[52] U.S. Cl. .................................................... 128/696
[58] Field of Search ............... 128/630, 696, 661, 702, 128/703, 704, 708, 709, 710

[56] References Cited

U.S. PATENT DOCUMENTS

| | | | |
|---|---|---|---|
| 3,123,768 | 3/1964 | Burch et al. ......................... | 128/710 |
| 3,215,136 | 11/1965 | Holter et al. ........................ | 128/702 |
| 3,267,934 | 8/1966 | Thornton ............................ | 128/704 |
| 3,561,430 | 2/1971 | Filler, Jr. et al. ................... | 128/661 |
| 3,598,112 | 8/1971 | Figar .................................... | 128/630 |
| 3,809,071 | 5/1974 | Davolos et al. ..................... | 128/702 |
| 3,830,228 | 8/1974 | Foner .................................. | 128/696 |
| 4,023,565 | 5/1977 | Ohlsson .............................. | 128/709 |
| 4,027,663 | 6/1977 | Fischler et al. ..................... | 128/710 |
| 4,197,854 | 4/1980 | Kasa .................................... | 128/630 |
| 4,367,753 | 1/1983 | Jirak .................................... | 128/708 |
| 4,422,459 | 12/1983 | Simson ................................ | 128/702 |

*Primary Examiner*—William E. Kamm
*Attorney, Agent, or Firm*—Benjamin J. Barish

[57] ABSTRACT

Signal processing apparatus particularly useful in electrocardiograph equipment comprises a conventional ECG amplifier channel, a high-gain ECG amplifier channel, signal averaging means, and a control panel enabling the manual selection, for inputting into the signal averaging means and outputting to the electrocardiograph, either the ECG signals from the conventional amplifier or those from the high-gain amplifier. The high-gain amplifier further includes a passive filter for removing the low-frequency components. According to another feature, the signal averaging means inlcudes a digital microcomputer providing time-base expansion; and according to a still further feature, the apparatus includes a further amplifier producing trigger pulses to the signal averaging means for triggering same, thereby enabling an optimum electrode configuration to be selected producing optimum triggering.

17 Claims, 5 Drawing Figures

SIGNAL PROCESSING APPARATUS AND HIGH RESOLUTION ELECTROCARDIOGRAPH EQUIPMENT INCLUDING SAME

BACKGROUND OF THE INVENTION

The present invention relates to signal processing apparatus for processing relatively weak electrical signals particularly to increase the signal-to-noise ratio. The invention is especially useful in electrocardiograph equipment, and is therefore described below with respect to this application.

ECG'S (electrocardiograms) are electrical potential traces accompanied by the contractions of the different cavities of the heart. They are an important aid in the study and diagnosis of abnormal heart activity. Particularly important in this respect is the His-Purkinje ECG (HPE) activity which, up to about ten years ago, could be recorded only by an invasive procedure in which an electrode was inserted into the heart by means of a catheter. In recent years, however, capabilities have been developed for detecting and recording HPE activity from the body surface by non-invasive procedures, but the techniques used for this purpose generally involve elaborate and expensive recording equipment which is not readily available at the clinical level. Therefore, non-invasive monitoring of HPE activity is generally limited to a few laboratories and has not become a standard cardiac test. Other cardiac activities extremely difficult or impossible to monitor by non-invasive techniques with present equipment include the discernment of the P-wave subcomponents which may denote various supraventricular structures, and the discernment of after-potentials which may herald ventricular fibrillation.

The previously known non-invasive systems for processing ECG signals particularly to monitor HPE activity generally use the well known signal averaging technique for enhancing the signal and reducing noise. Signal averaging increases the signal-to-noise ratio of repetitively occuring data by serially adding together the repetitive signals, each addition being initiated by a synchronizing signal providing a reference or fiducial point having a constant time relation to the data signal. Thus, the coherent portions of the signal (data) reinforce each other with each successive addition, whereas the non-coherent portions (noise) add out-of-phase and therefore tend to cancel out with each successive addition. The quality of the synchronizing or triggering point for each addition cycle is critical to the quality of the averaging process, since any variation in time between the signal of interest and the fiducial or reference point, referred to as jitter, will rapidly degrade the produced average signal.

BRIEF SUMMARY OF THE INVENTION

An object of the present invention is to provide signal processing apparatus which is particularly useful in cardiography. Another object of the invention is to provide electrocardiograph equipment which may be constructed at relatively low cost and which provides a plurality of options for the non-invasive detection, monitoring, and recording of HPE activity and other activities heretofore difficult or impossible to monitor by noninvasive techniques.

According to one broad aspect of the present invention, there is provided signal processing apparatus particularly useful in electrocardiograph equipment for processing ECG signals detected by electrodes placed against the subject's body, comprising: (A) data amplifier means including: (1) a first amplifier receiving the detected ECG signals from the electrodes and producing first amplified ECG data signals, and (2) a second amplifier, having a substantially higher gain than the first amplifier, also receiving the detected ECG signals from the electrodes independently of the first amplifier and producing second amplified ECG data signals, (B) signal averaging means; and (C) a control panel including means enabling the manual selection, for inputting into the signal averaging means and outputting to the electrocardiograph, either the first amplified ECG data signals from the first amplifier, or the second amplified ECG data signals from the second amplifier.

The described apparatus further includes a filter removing the low-frequency components of the amplified ECG data signals outputted from the second amplifier, which filter is a passive one and includes means for preselecting the frequency range of the components removed from the amplified ECG data signals. It has been found that in such an arrangement, including a passive (rather than active) filter, there is no production of ringing artifacts, i.e., spikes produced by the machine itself rather than by the subject.

According to another feature of the present invention, the signal averaging means includes: a digital microcomputer; an analog-to-digital converter for converting the analog data from the selected amplifier to digital form before being applied to the microcomputer; and a digital-to-analog converter for converting the digital data from the microcomputer to analog form before being outputted to the electrocardiograph; the digital microcomputer being programmed to output its digital information to the digital-to-analog converter at a fraction of the speed at which it inputs its information from the analog-to-digital converter, thereby providing time-base expansion of the inputted data. The provision of such a time-base expansion feature improves the frequency response without changing the mechanics of the cardiograph. Thus, by including this feature in the signal processing apparatus, such apparatus can be used with a conventional cardiograph, without changing the mechanics of the recording device thereof, and still provide better frequency response.

According to a still further aspect of the invention, the apparatus further includes a triggering circuit having a further amplifier receiving the detected ECG signals from the electrodes independently of the data amplifier means, and producing trigger pulses therefrom; and means for feeding the trigger pulses to the signal averaging means for triggering same, whereby the electrode configuration producing optimum triggering as applied to the triggering circuit can be selected from the control panel independently from the electrode configuration producing optimum ECG data signals as applied to said data amplifier means.

According to a still further aspect of the invention, the apparatus further includes: an R-wave detector receiving the amplified ECG data signals from the data amplifier means and producing an output pulse having a duration corresponding to the duration and/or amplitude of each R-wave thereof; comparator means for comparing the output pulses with an average value representing the average of a plurality of the R-waves to determine whether the respective ECG complex represents an extra systole; and means for rejecting each ECG complex representing an extra systole from being included in the signal averaging process.

According to a still further aspect of the invention, the apparatus further includes an RMS measuring circuit connected to the output of said data amplifier means and converting the amplified ECG data signals therefrom to RMS values; and a comparator comparing said RMS values with a reference level and effective to reject from the averaging process each ECG complex whose RMS level exceeds that of the reference level.

According to a still further feature, the present invention further includes means for measuring the effective resistance of each of the configurations of electrodes as applied against the subject's body.

Further features and advantages of the invention will be apparent from the description below.

BRIEF DESCRIPTION OF THE DRAWINGS

The invention is herein described, by way of example only, with reference to the accompanying drawings wherein.

DESCRIPTION OF A PREFERRED EMBODIMENT

General Construction

Figure 1:
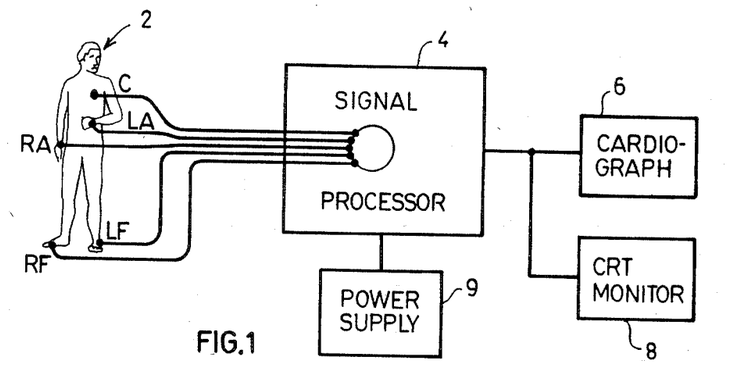
FIG. 1 is a block diagram illustrating one form of electrocardiograph equipment incorporating the present invention.

With reference first to FIG. 1, there is illustrated electrocardiograph equipment including a plurality of electrodes, generally designated 2, which may be of conventional construction adapted to be placed against the subject's body according to the various conventional configurations to detect ECG signals. Thus, in FIG. 1 the electrode system 2 includes right-arm electrode RA, left-arm electrode LA, right-foot electrode RF, left-foot electrode LF, and chest electrode C. These electrodes are connected to a signal processing unit, generally designated 4, which processes the detected ECG signals and feeds them to a cardiograph unit 6 for recording the processed signals. The illustrated equipment further includes a CRT monitor unit 8 for displaying the processed signals, and a power supply 9 for supplying the power to the signal processor 4, the cardiograph 6 and the monitor 8.

The cardiograph unit 6 may be of conventional construction as now available, or it may be incorporated into the novel signal processor unit 4. Thus, it is contemplated that the signal processor unit 4 can be constructed as a separate unit for interfacing with conventional cardiograph equipment, or as a consolidated unit embodying such cardiograph equipment.

Briefly, the signal processor unit 4 includes a mode selector for selecting a real-time mode wherein the detected ECG signals are displayed in real time, or an averaged time mode wherein the detected ECG signals are enhanced by an averaging technique performed by a digital microcomputer. The signal processor 4 further includes three amplifiers, namely a conventional-gain data amplifier, a high-gain data amplifier, and a trigger-pulse-producing amplifier, and various other means for optimizing the averaged signal when the system is operating according to that mode, and also for increasing the resolution of the real-time signals when the system is operating according to the real-time mode. All information stored in the microcomputer is read-out at a much slower rate than that at which the information is inputted into the microcomputer to provide time-base expansion, in this case by a factor of "8". The foregoing features, as well as others included in the signal processing unit 4 of FIG. 1, are described more particularly below with respect to the block diagram of that unit as illustrated in FIG. 3, and the control panel of that unit as illustrated in FIG. 2.

Figure 2:
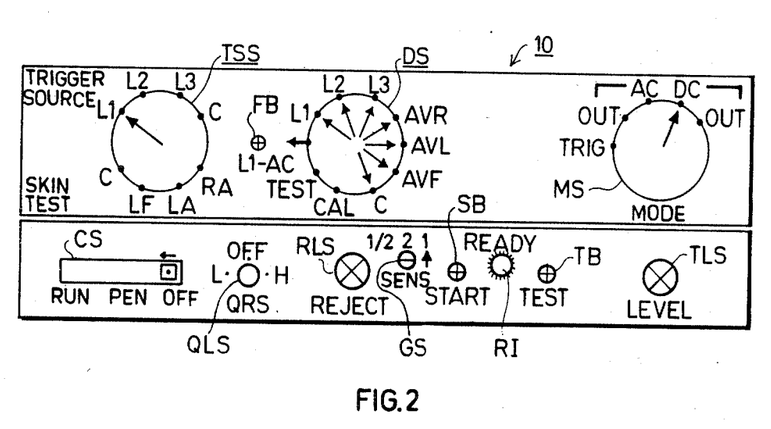
FIG. 2 illustrates the control panel in the signal processing portion of the system of FIG. 1.
Figure 3:
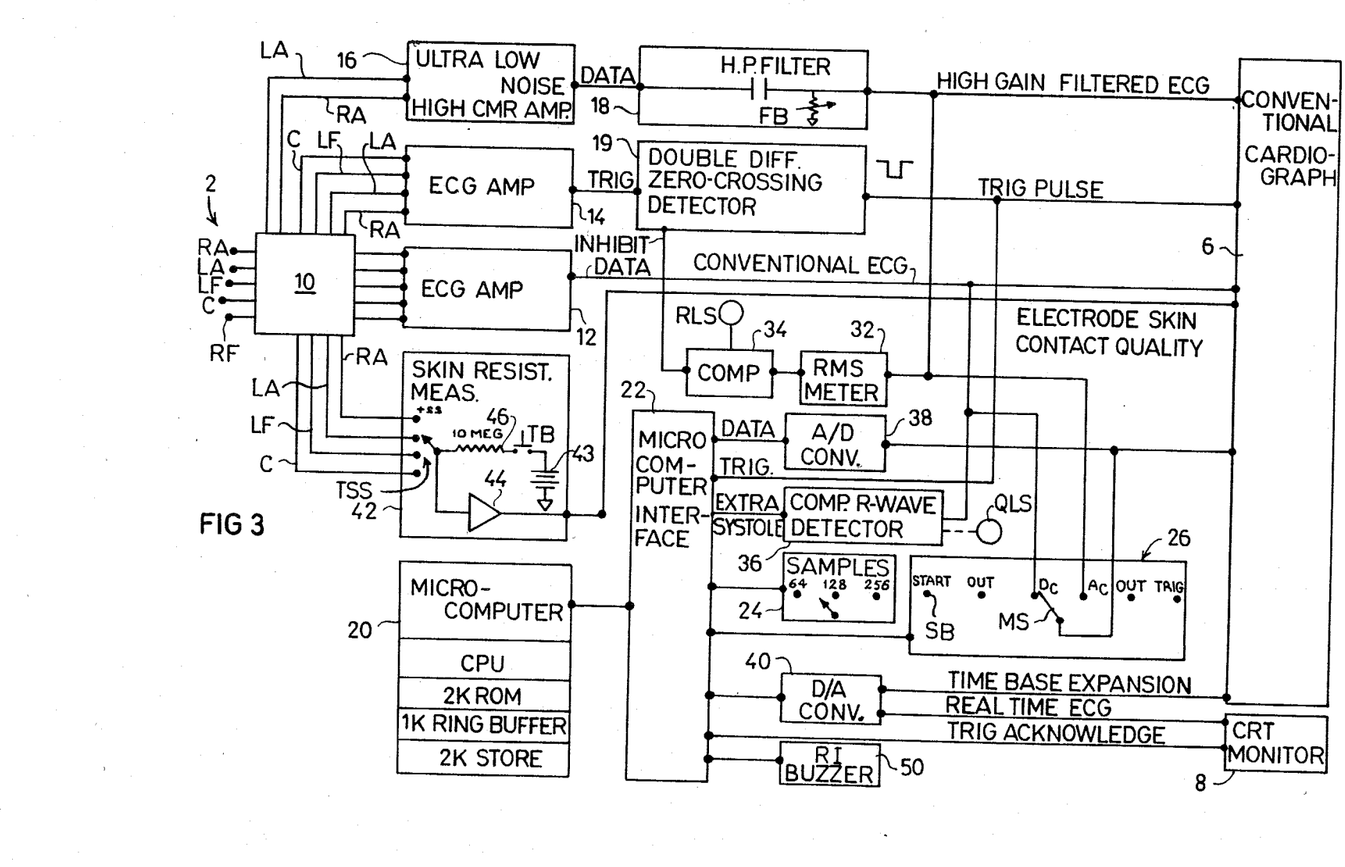
FIG. 3 is a block diagram of the signal processing apparatus of the electrocardiograph equipment illustrated in FIG. 1.

Control Panel of FIG. 2

FIG. 2 illustrates the control panel, generally designated 10, for the signal processor unit 4 of FIG. 1. At the upper part of the control panel, there are provided three selector knobs, namely a mode selector MS, a data selector DS and a trigger-source selector TSS. Between the latter two knobs is provided a smaller knob FB, effective to preset the filter band-pass of the high-gain amplifier, as will be described more particularly below.

The lower part of the control panel 10 illustrated in FIG. 2 includes several additional knobs, namely a trigger-level selector TLS, a gain selector GS, a reject-level selector RLS, and a QRS-level selector QLS. The lower portion of the control panel 10 further includes a Start button SB, a test button TB, a "Ready" indicator RI, and a cardiograph control switch CS. Selection between the real-time mode or averaged-time mode of operation is effected by the Start button SB. If that button is not depressed, the apparatus operates according to the real-time mode; but when button SB is depressed, this clears the microprocessor and starts the averaging process. Completion of the averaging process, i.e., the accumulation of the preselected number of ECG complexes to be averaged, is indicated by the "Ready" indicator RI and by a buzzer.

Mode selector MS has five positions, as follows:

(1) The DC-position is selected when it is desired to process the detected ECG signals in a conventional manner, wherein the conventional-gain amplifier is used, the frequency response of which is from 0.05–400 Hz. If the apparatus is operating according to the averaging mode, initiated by the pressing Start button SB as described above, the apparatus will accumulate and average 64 ECG complexes, at which time the "Ready" indicator RI is energized, and at the same time a buzzer is sounded.

(2) The OUT-position in the clockwise direction of the DC-position of mode selector MS is selected when it is desired to read-out the average of the 64 complexes accumulated during the DC mode. When knob MS is in this OUT position, the stored and averaged 64 complexes thus accumulated are fed from the microcomputer included within the signal processing unit 4 to the cardiograph unit 6 and the monitor 8.

(3) The AC-position of mode selector MS is selected when the apparatus is to be operated according to a high-resolution mode wherein the high-gain amplifier is used, when the Start button SB is depressed for an averaged-time mode of operation, the apparatus accumulates 128 complexes in this AC mode, rather than 64 complexes in the above-described DC mode. In addition, when the apparatus is operated according to the AC mode, the high-gain amplifier increases the gain by a factor of 1000 over the gain in the conventional DC mode; in addition, the data is filtered by a variable high-pass filter to pass frequencies within the range of about 15–500 Hz. The frequency passed can be preset by knob FB. During the averaging mode, when 128 complexes have been accumulated, this is also signalled by the energization of the Ready indicator RI and the buzzer as described above with respect to the DC-mode of operation.

(4) The OUT-position of mode selector MS, in the counter-clockwise direction of the AC-position, is selected after the accumulation of the 128 complexes has been complete as signalled by indicator RI and the buzzer, whereupon the accumulated averaged complex is fed from the microcomputer to the cardiograph unit 6 and to the monitor 8 for display.

(5) TRIG-position is selected when the triggering of the microcomputer is to be preset for the averaging process by adjusting the trigger level selector TLS, in the manner to be described more particularly below. This position on the mode selector MS is also selected when it is desired to average 256 complexes, rather than 128, in order to improve the signal-to-noise ratio of the averaged signal.

The data selector knob DS includes the standard eight positions conventionally provided in a cardiograph, namely positions $L_1$, $L_2$, $L_3$, AVR, AVL, AVF, C (chest) and CAL (calibration). It further includes the position TEST to perform a test operation, and the position $L_1$-AC, to operate the apparatus according to a high-resolution mode involving the variable high-pass filter circuit mentioned earlier which circuit is adjusted by knob FB on the control panel.

The trigger source selector knob TSS on the control panel 10 illustrated in FIG. 2 selects the electrodes, or electrode configuration, for triggering the microcomputer to optimize the averaging process, and also for making impedance tests in order to determine the quality of the skin-electrode contacts. Thus, positions $L_1$, $L_2$, $L_3$ and C refer to the conventional electrode configurations in a standard cardiograph. Trigger source selector TSS also includes four additional positions for separately selecting the right-arm electrode RA, left-arm electrode LA, left-foot electrode LF and chest electrode C, which selections are particularly used in testing the skin-electrode impedance of each of these electrodes.

Whenever the apparatus is operating during a mode in which the microcomputer reads-in a number of complexes, stores them and then reads them out (e.g., during either of the AC or DC averaging modes initiated by depressing the start button SB), the computer is preprogrammed to effect a time-base expansion of the information. In this case, the time-base expansion is of a factor of "eight". Thus, the data is read into the microcomputer at a first speed, and is read out of the microcomputer to the cardiograph unit 6 or monitor 8 at a speed which is 1/8th of the input speed. In the example to be described below, the input speed into the microcomputer is 1000 samples/second; and the output speed is 125 samples/second. Thus, at standard cardiograph paper speed of 25 mm/sec, the virtual frequency response is increased from 100 to 800 Hz, and the time base resolution is increased from 40 ms/mm to 5 ms/mm.

The Test button TB is depressed whenever it is desired to make a skin-electrode impedance test of an electrode as selected by the operation of the trigger source selector TSS. Test button TB may also be used for monitoring a predetermined number of the ECG complexes detected without averaging. Thus, if Test button TB is depressed while the apparatus is operating according to the averaging-time mode, effected by depressing the Start button SB as described above, the microcomputer clears all the complexes previously accumulated, and then accumulates the ECG complexes for a predetermined time interval, in this case for three seconds which is about three complexes. When this accumulation is completed, the "Ready" indicator RI, and also a buzzer, are energized to signal this to the user. The user then moves the mode selector switch MS to the AC-OUT position, whereupon the ECG complexes stored during this "test" interval will be read out to the cardiograph 6 and to the monitor 8 without averaging. However, this read-out of the accumulated complexes will be with the above-mentioned time-base expansion, which is effective whenever reading-out computer-stored data, wither during the AC or DC modes of operation of mode selector MS, as briefly described above, and as to be described more particularly below.

The control panel 10 further includes the conventional cardiograph control switch CS.

The above-mentioned controls performed by the control panel 10 illustrated in FIG. 2 will be more particularly described below with respect to the block diagram illustrated in FIG. 3, and several specific operations performed by the use of this apparatus.

Block Diagram of FIG. 3

FIG. 3 is a block diagram illustrating the signal processor unit 4, which as mentioned above, receives the ECG signals detected by the electrodes 2 in FIG. 1, processes this information according to various selectable modes and controls, and then outputs the processed information to the cardiograph unit 6 and the monitor unit 8, which latter units may be of conventional construction.

The signal processor unit 4 includes three amplifier channels all selectably connectable to the electrodes 2. These channels include a conventional ECG amplifier 12, a second conventional ECG amplifier 14, and an ultra-low-noise high-CMR (common mode rejection) differential amplifier 16. Amplifier 12 is used for amplifying the ECG signal detected by electrodes 2 in a conventional manner for outputting data signals to the conventional cardiograph 6 and also to the microprocessor for averaging, as to be described below; whereas amplifier 16 is effective to amplify the ECG signals at a substantially higher gain (e.g., increased by 1000) than amplifier 12. The signals from amplifier 16 are applied to a variable high-pass filter 18 before application to the conventional cardiograph 6 or to the signal-averaging microprocessor. The selection of either the conventional amplifier 12 or the ultra-low-noise amplifier 16 is effected from the control panel 10, particularly by the mode selector MS, and the gain of the selected amplifier 12 or 16 may be further varied by gain selector knob GX, which may be preset to any one of three positions (½, 2, 1). The same selector also controls the gain of the conventional cardiograph 6 in a corresponding manner.

Amplifier 14 is also a conventional ECG amplifier, similar to amplifier 12, but it is used for supplying the triggering pulses to the signal averaging circuit which averages the ECG data signals from amplifier 12. Thus, amplifier 14 is always selected during an averaging process, and its output is supplied to a double-differentiator zero-crossing detector circuit 19 which detects the zero-crossing of the second derivative of the R-wave of the ECG signal from amplifier 14 to produce a trigger pulse at the point of maximum slope of the R-wave. These trigger pulses are supplied with the data signals (from the selected amplifier 12 or amplifier 14) to the cardiograph unit 6, and also to the averaging circuit.

The averaging circuit includes a microcomputer 20 and an interface unit 22. Micro-computer 20 may be a standard unit which has been programmed to perform the various machine operations as will be described more particularly below, including the averaging of the ECG data signals from the conventional amplifier 12 or the ultra-low-noise amplifier 16, according to the selection made.

As described earlier, if the averaging mode is desired, the Start button SB on the control panel (FIG. 2) must be depressed, which starts the averaging process. If button SB is not depressed, the apparatus will operate according to the non-averaging, or real-time, mode wherein the detected ECG signals are fed to the cardiograph unit 6 for recording, and to the monitor unit 8 for display.

As also briefly described earlier, the mode selector MS determines whether the apparatus operates according to the DC mode, wherein the conventional amplifier 12 is effective, or according to the AC mode, wherein the high-gain amplifier 16 including the variable high-pass filter 18, is effective. The data selector knobs DS on the control panel 10 enables the user to select the specific one of the various electrode configurations that will be made effective to supply the detected ECG signals to the selected amplifier 11 or 16; and the trigger source selector TSS on the control panel 10 enables the user to select the electrode configuration to supply the ECG signals to amplifier 14 for producing the triggering pulses used in the signal averaging process with respect to the data signals from either amplifier 12 or 16. The foregoing is schematically indicated by the control panel block 10 in FIG. 3 between the electrodes 2 and the three amplifiers 12, 14 and 16. It will thus be seen that a different electrode configuration may be selected for supplying the triggering pulses than the electrode configuration selected for supplying the data signals. This capability of the system is very important, as will be described more particularly below, in enabling the selection of an electrode configuration providing optimum data signals, and another electrode configuration providing optimum triggering pulses for use in the signal averaging process.

As shown schematically in FIG. 3, the mode selector switch MS determines whether the apparatus will operate according to the DC mode, wherein the ECG data signals from the conventional amplifier 12 are processed (in real time or averaged-time), or whether the signals from the high-gain amplifier 16 will be processed. Whichever channel is selected, the ECG signals from the respective channel are directed to the cardiograph 6 for recording, and also to an analog-to-digital converter 38 for conversion to digital form before being fed into the microcomputer 20 via its interface unit 22.

Microcomputer 20 may be a commercially available unit, such as the Intel 8085, which includes a CPU (central processor unit), a 2K ROM (read only memory), a 1K ring buffer, and a 2K storage. It is pre-programmed to perform an averaging process in a known manner, for enhancing the detected ECG signals by adding the coherent signal portions and effectively cancelling the non-coherent noise portions. As indicated earlier, if the averaging process is performed while the mode selector MS is in its DC-position, then 64 ECG complexes are averaged. On the other hand, if the averaging occurs in the AC-position of selector MS, 128 complexes are averaged; and if it occurs in the TRIG-position, 256 complexes are averaged. The foregoing selection of the number of samples is schematically indicated by box 24 in FIG. 3 connected to the microcomputer interface unit 22.

Box 26 in the block diagram of FIG. 3 schematically illustrates the functions performed by the mode selector MS as described above. This box 26 also schematically illustrates the function performed by the start button SB on the control panel 10 for starting the averaging process by causing the microcomputer 20 to store a predetermined number of the ECG complexes, as specified by box 24 described above. Upon the completion of the storing of the specified number of complexes, the ready indicator RI on the control panel is energized, and also a buzzer is energized, both of the latter being schematically indicated by box 50 in FIG. 3. As described above, when the accumulation has been completed in the microcomputer, the averaged signal is outputted, by positioning the mode selector MS to either of the OUT-regulator positions, to the cardiograph unit 6 and also to the monitor 8.

The variable high-pass filter 18, from the high-gain amplifier 16, is a passive filter removing the low-frequency components of the amplified ECG signals. This filter is varied by knob FB on the control panel of FIG. 2, which knob changes the time constant of the R-C filter within Box 18 of FIG. 3. The gain of the high-gain amplifier 16 is controlled by the 3-position knob GS on the control panel 10 of FIG. 2. The "filter corner frequency" of this high-gain channel is adjustable, also from the control panel by knob FB, to obtain an optimum high-resolution trace in the cardiograph unit 2 and also in the monitor 8.

As an example, in a conventional system the time based resolution is about 400 ms/cm, and the amplitude resolution is about 1 mV/cm; whereas in the system illustrated in the drawings, the time based resolution may be increased by a factor of 8 to 50 ms/cm, and the amplitude resolution may be increased by a factor of 100 or better.

The illustrated system also includes an arrangement for rejecting the defected ECG signals when the high-gain amplifier 16 is selected and the background noise increases above a preset level; for example, during the inspirium, the noise increases sharply due to respiratory muscle activity. For this purpose, the high-resolution channel including the high-gain amplifier 16 and filter 18 outputs their signals to an RMS metering circuit 32, which compares the RMS level of the detected signal with a reference level in a comparator 34. This reference level may be preset from the control panel of FIG. 2 by Reject-knob RLS. When the detected RMS level exceeds this reference level, comparator 34 outputs an "inhibit" pulse to the trigger circuit, namely to the zero-crossing detector 19, to inhibit the outputting of a trigger pulse at that time, thereby excluding the respective ECG complex from the averaging process.

The system illustrated in FIG. 3 further includes an arrangement for rejecting any detected extra systoles appearing in the conventional amplifier channel during the averaging process. Thus, the output of the conventional-gain amplifier 12 is also fed to a comparator 36, which tests to see whether each incoming R-wave is derived from a normal ECG complex, or from an extra systole. If it is determined to be an extra systole, it so informs the microcomputer 20 via its innerface 22 so that the extra systole will not be included in the averaging process.

Comparator 36 of FIG. 3 is controlled by knob QLS on the control panel illustrated in FIG. 2. Thus, this knob can be set to any one of three positions, namely an "off" position wherein this "extra-systole-rejection" function is disabled; the "L" position, wherein a large change (e.g., 25%) in the detected QRS complex causes rejection; or the "H" position, wherein a small change (e.g., 12%) in the detected QRS complex causes rejection.

As indicated earlier, the illustrated system also provides for "time-base expansion" of the information processed by the microcomputer 20. For this purpose, the microcomputer 20 is preprogrammed so as to operate analog-to-digital converter 38 to read the information into the computer at a substantially higher rate than that at which the digital-to-analog converter 40 reads out the information. For example, analog-to-digital converter 38 may be operated at a read-in rate of 1000 samples/second, and digital-to-analog converter 40 may be operated at a read-out rate of 125 samples/second, thereby providing a time base expansion of the factor of "8". This increases the virtual frequency response from 100 to 800 Hz and the time-base resolution from 40 ms/mm to 5 ms/mm using a standard cardiograph paper speed of 25 mm/s.

As shown in FIG. 3, the digital-to-analog converter 40 outputs the process information with the above-described time-base expansion to the cardiograph unit 6. This converter also outputs the processed information to the monitor unit 8 in real time.

The trigger pulse produced by the trigger channel including amplifier 14 and zero-crossing detector 19 is applied to the microcomputer 20 via its interface unit 22. These trigger pulses, derived from the R-waves, are used for triggering the microcomputer while it is performing the digital averaging process.

These trigger pulses are also used for indicating the quality of the triggering, which can greatly affect the quality of the averaging process since any variation in the trigger point will rapidly degrade the produced average signal. Thus, as shown in the block diagram of FIG. 3, the monitor unit 8 receives a "trigger acknowledge" signal from the microcomputer 20 via its interface 22. Since the averaging process performed by the microcomputer requires a delay routine, the real time ECG signals outputted from the microcomputer via the digital-to-analog converter 40 will actually appear after a delay (e.g., 200 ms). However, when the microcomputer outputs the "trigger acknowledge" signal to the monitor unit 8, this is done without delay. The CRT monitor unit 8 sweep begins with this trigger. Accordingly, if the trigger is not always produced at the same point of the R-wave, the CRT monitor unit 8 will display a "jittery" R-wave, thereby indicating a poor triggering performance.

The quality of the trigger pulses can be improved by selecting the optimum electrode configuration by means of the trigger source knob TSS in the control panel of FIG. 2, as indicated earlier, since this knob controls the electrode configuration to be applied to the trigger-producing amplifier 14. Thus, if it is seen that one selected electrode configuration provides poor triggering quality (e.g., apparent by the above-described "jittering" on the monitor unit 8), a different electrode configuration can be selected by trigger selector knob TSS. The trigger level knob TL on the control panel illustrated in FIG. 2 is used for preselecting the threshhold value of the trigger signal. Normally, it is adjusted until the ECG display on the monitor unit 8 is steady.

As indicated earlier, the electrode configuration for receiving the ECG data signals is selected by data selector knob DS, which includes the standard 8 positions of the conventional cardiograph. This selector, however, includes two additional positions, namely TEST and $L_1$-AC. The TEST-position is used for testing the skin-electrode resistance, as will be described below; and the $L_1$-AC position is used for selecting only the $L_1$ electrode configuration, i.e., electrodes LA and RA, which configuration is the effective one when the system is operating with the high-resolution channel including the high-gain amplifier 16 and the variable high-pass filter 18.

Testing for skin-electrode resistance is done by depressing the Test-button TB. This test button, however, is also used for performing a non-averaging process wherein a predetermined number of ECG complexes are accumulated and then displayed. The predetermined number is preprogrammed into the microcomputer 20; in this case, it is the number occuring during 3 seconds. Thus, when Test button TB is depressed, the microcomputer accumulates the ECG complexes for 3 seconds (usually 3 complexes) whereupon the "Ready" indicator RI will be illuminated. These accumulated complexes may then be read-out by moving knob MS to the "OUT" position, whereupon the accumulated ECG complexes will be read out without averaging, but with the above-described time-base expansion.

The system illustrated in FIG. 3 further includes a skin-electrode resistance measuring circuit, included within block 42, for measuring the electrical resistance between the reference electrode (namely the right foot electrode RF and each of the other electrodes). This circuit includes the test button TB of the control panel illustrated in FIG. 2, a source of voltage 43 (e.g., 2.5 volts), an amplifier 44, and a large resistor (e.g., 10 Meg) 46. The resistor 46 forms a voltage divider with the skin-electrode resistance of the electrode configuration selected by the selector knob TSS, this resistance being amplified in amplifier 44 and fed to the cardiograph unit 6.

Following is a description of a number of specific operations that may be performed by the use of the illustrated apparatus:

Recording Conventional ECG

For conventional ECG recording, the electrodes are to be applied to the patient as illustrated in FIG. 1. The mode selector MS on the control panel illustrated in FIG. 2 should be positioned to the DC position, and the trigger source TSS may be positioned to the $L_1$ position. The conventional 12-lead cardiogram can now be recorded by using the cardiograph switch CS and using the data selector DS to select the electrode configurations. The respective cardiograms will be recorded in the cardiograph unit 6 and will be displayed in the monitor unit 8 in the conventional manner.

Recording Averaged ECG (ACG)

As indicated earlier, the microcomputer 20, which performs the averaging process by preprogramming in accordance with known procedures, employs the R-wave for triggering purposes, i.e., for producing the synchronizing signals providing the reference or fiducial point having a constant time relation to the data signal during the repetitive addition performed by the signal averaging process. The illustrated apparatus, as described earlier, permits selection and adjustment of the triggering source, independently of the data source, to provide optimum averaging results.

The selection of the triggering source is performed by the trigger source selector TSS. First, the mode selector MS should be positioned to the TRIG-position, and the Reject level selector RL should be "off". The trigger source selector TSS may then be located to the $L_1$ position, and the trigger level knob TLS may then be rotated clockwise until a steady triggering pulse is displayed in the electrograph unit 6.

If it is desired to include the RMS-background Reject feature described above, the Reject knob RSL may be rotated clockwise until about one-half of the heartbeats fail to evoke a triggering pulse. This will have the result of causing the RMS measuring circuit 32 and comparator circuit 34 (FIG. 3) to inhibit the production of trigger pulses to the microcomputer 20 during this excessive background noise condition, so that the computer will thereby reject from the averaging process the ECG complexes appearing during excessive background noise conditions, e.g., during the inspirium when muscle activity increases the background noise.

If it is desired to reject the extra-systoles from the averaging process as described above, this can be done by presetting the selector QLS on the control panel of FIG. 2 either to its L-position or H-position. In either of these positions, the comparator circuit 36 of FIG. 3 is made effective to cause the microcomputer to learn the normal QRS waveform and to reject from the averaging process abnormal QRS complexes, i.e., extra systoles. This is done by the comparator 36 in the block diagram of FIG. 3, which produces an output pulse having a duration corresponding to the duration and amplitude of each R-wave. Such output pulses are compared with an average value in the computer representing the average of a plurality of such R-waves, to determine whether the respective ECG complex represents an extra systole; if so, that complex is not included in the averaging process.

Presetting knob QLS to the L-position (low), causes rejection when there is a 25% change in the QRS-duration; and when it is in the H-position (high), a 12.5% change will cause rejection.

Whenever an ECG complex is rejected, either because it appears with excessive background noise or because it represents an extra-systole, this fact is signalled to the user by the energization of the light indicator on the control panel and the sounding of the buzzer 50 (block diagram of FIG. 3).

The apparatus also permits the user to view the quality of the triggering pulse and to select a different electrode configuration for producing the triggering pulses to improve the quality if desired. Thus, assuming the trigger source selector TSS is positioned to select configuration $L_1$, whereas the data selector knob is also positioned at its position $L_1$, the data ECG signals derive from the data amplifier 12 (or the high-gain amplifier 16 if this mode is selected) will be displayed on the monitor unit 8 at a delay (of approximately 200 ms) because of the averaging process performed by the microcomputer 20. However, the trigger pulses derived from the trigger amplifier 14 trigger the sweep on monitor 8 without a delay. Thus, if the trigger pulses are not always produced at the same point of the R-wave, the display appearing on the monitor unit 8 will be jittery, which will be apparent to the user. When this occurs, the user can select a different electrode configuration, by the use of the trigger source selector TSS, to select a different electrode configuration producing more stable triggering pulses, which will be apparent by the absence of jitter on the monitor display unit 8. The apparatus thus enables the user not only to view the quality of the triggering pulses in the averaging process, but also to select the electrode configuration providing the best quality. As indicated earlier, the quality of the averaging process depends to a great extent on the quality of the triggering pulses.

The user may then select the mode of operation by the use of the mode selector knob MS. By setting the knob to position DC, the conventional amplifier 12 is made effective providing a frequency response of 0.05 to 400 Hz, and providing an averaging of 64 ECG complexes. Any conventional ECG electrode configuration, as selected by the data selector knob DS may be averaged in this DC-mode.

On the other hand, if higher resolution is desired, mode selector MS may be set to the AC-position, whereupon the high-gain amplifier 16, and its variable high-pass filter 18, are made effective. This increases the frequency response to 15-400 Hz, this being adjustable by adjusting filter band-pass knob FB. The AC-mode also increases the gain, E.G., by a factor of about 1000, and causes the microcomputer 20 to accumulate 128 ECG complexes during the averaging process. The gain may be preselected by gain-selector knob GS.

If a larger number of complexes is desired to be accumulated, mode selector MS may be set to the TRIG-position, wherein it will accumulate 256 complexes during the averaging process.

To start the averaging process, under any of the above modes, the Start button SB on the control panel is depressed. This causes the microcomputer 20 to clear, and to begin averaging the specified number of complexes. When the specified number has been accumulated, the READY indicator RI is energized to signal to the user that the averaging process has been completed.

The averaged ECG complex is now stored in the computer memory. To obtain a hard copy via the cardiograph unit 6, the mode selector MS is moved to the OUT-position, either DC or AC, according to the mode selected.

The averaged information in the microcomputer will now be read-out to the cardiograph unit 6 but at a slower rate than read-into the cardiograph, to provide a time base expansion. As described earlier, if a time-base expansion of the factor of "8" is desired, the read-in speed of operation of the read-in analog-to-digital converter 38 may be about 1000 samples per second, and the read-out speed of the digital-to-analog converter 40 may be at about 125 samples per second. The control of the two converters 38 and 40 provide this time-base expansion may be preprogrammed into the microcomputer 20 according to known techniques.

Recording High Resolution Cardiagram (HRC)

The manner of operating the apparatus to produce high resolution cardiagram recording of the averaged data signals, derived from the high-gain amplifier 16 and filter 18, is described above, wherein it was pointed out that the computer will average either 128 or 256 complexes, as determined by setting the mode selector knob MS in either the AC-position or the TRIG-position, respectively. In this high-resolution recording of the averaged data signals, the data selector knob DC should be in the $L_1$-AC position. When the Start button SB is depressed, the P-R segment of each ECG complex will be displayed on the monitor unit 8, and knob FB may be adjusted to obtain an optimal trace. Thus, as the knob is turned clockwise, this increases the frequency of the signal components removed by the variable filter 18 of FIG. 3; therefore, the P-Q segment becomes flatter, but the signal of interest is diminished. The P-R segment, as displayed in the monitor 8, should not be saturated. Noisy ECG traces can be eliminated by the reject knob RL, which adjusts the threshhold of comparator 34 of FIG. 3 to inhibit the ECG signals present with excessive background noise. As indicated earlier, the gain of the high-resolution amplifier 16 can be modified by the sensitivity-level knob GS.

To produce an averaged output during this high-resolution mode, the start button SB is depressed as described earlier, whereupon the microcomputer 20 accumulates and stores the specified number of complexes, signalled by the energization of the Ready-light RI and buzzer 50 (FIG. 3), whereupon the user may move the mode selector knob MS to the OUT-position for reading out the averaged signals to the cardiograph unit 6 with time-base expansion as described earlier.

Recording Multiple-Complexes Without Averaging

The illustrated apparatus also includes the capability of recording and displaying a selected number of ECG complexes, both of the conventional-resolutional type derived from amplifier 12 and of the high-resolution type derived from amplifier 16 and filter 18 but without averaging. For this purpose, the mode selector MS, the data selector DS and the trigger selector TS are used in the manner described above for selecting the mode of operation, and the electrode configuration for producing the data signals and the triggering pulses. The TEST-button TB is then depressed, whereupon the microcomputer 20 clears the computer and accumulates the ECG data signals for a period of three seconds, at which time the READY-light RL is energized. During this time, the computer displays the accumulated P-R intervals on the monitor unit 8, so that if the data is not satisfactory, the appropriate adjustment can be made as described earlier. When the data is satisfactory, the mode selector MS is then turned to the OUT-position, whereupon the information will be outputted to the cardiograph unit 6 without averaging but with the time-base expansion as described earlier.

Some Test Results

Figure 4:
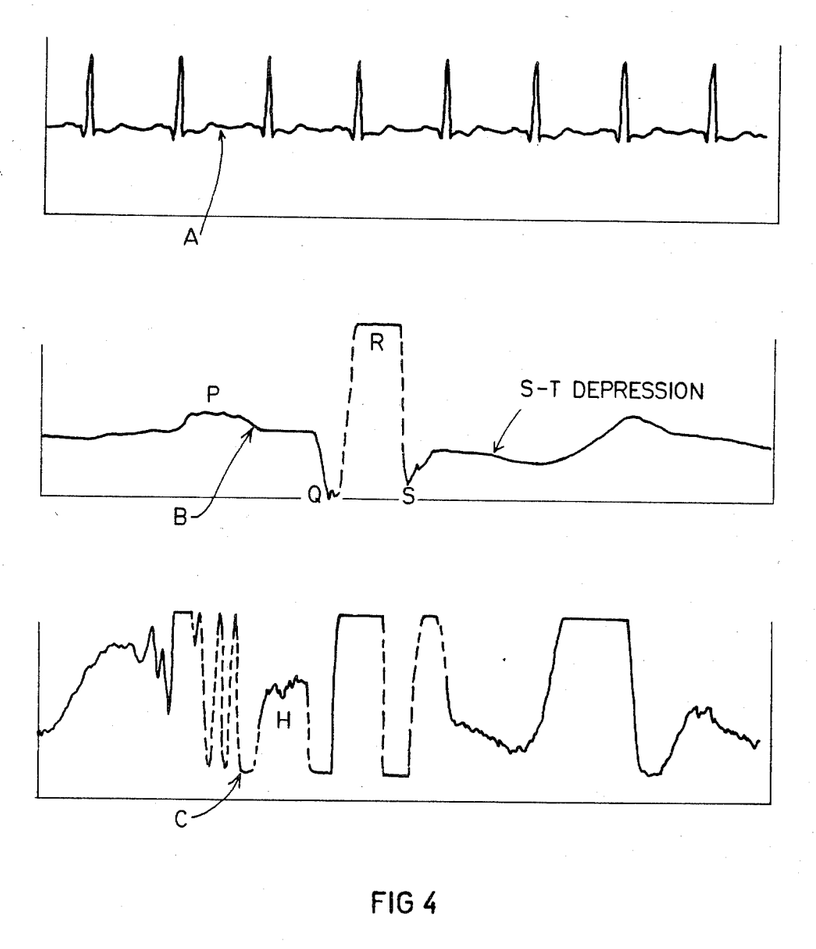
FIGS. 4 and 5 illustrate various waveforms produced by the use of the equipment illustrated in the drawings.
Figure 5:
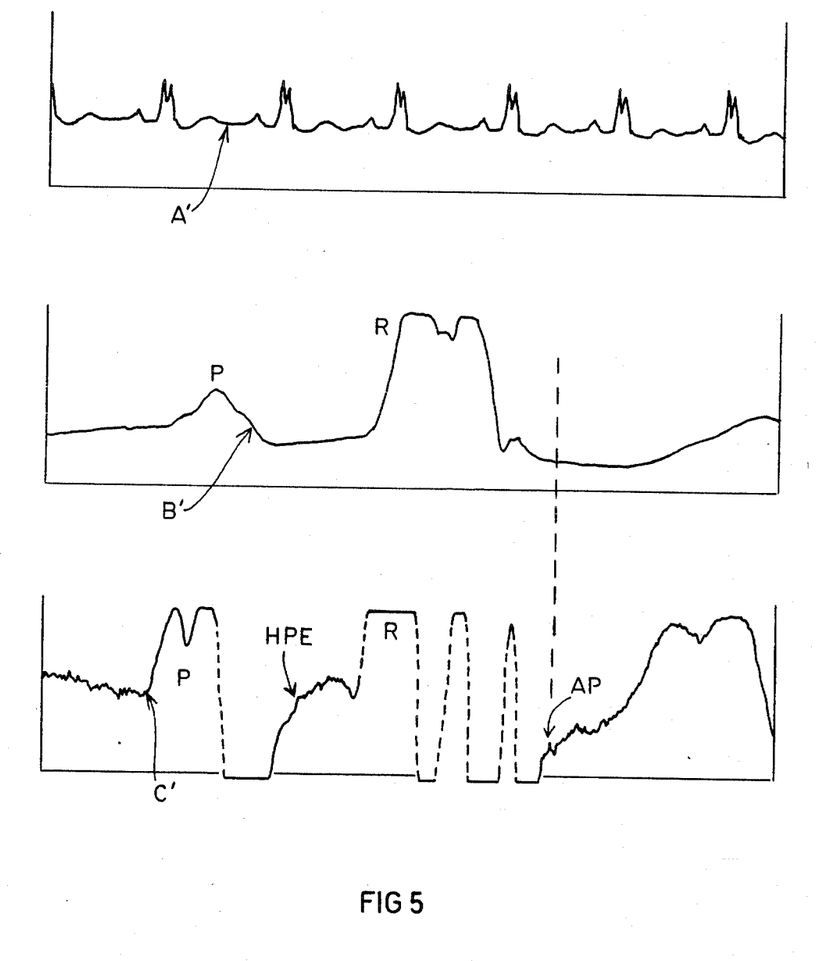

Some test results obtained by using the above-described apparatus are illustrated in FIGS. 4–6.

With reference to FIG. 4, curve A illustrates test results obtained by operating the apparatus according to the conventional ECG-mode (DC-position of mode selector MS), with a conventional cardiograph unit 6 having a paper speed of 25 mm/s, a real frequency response of 0.07–100 Hz, a time base resolution of 400 ms/cm, and an amplitude resolution of 1 mV/cm. Curve B illustrates the results produced when the apparatus is operated to output the averaged ECG data signals, by selecting the DC-position mode of mode selector MS, wherein it will be seen that, although the same conventional cardiograph 6 is used, the frequency response is increased from 0.07 to 700 Hz (because of the time-base expansion), the time base resolution is increased to 50 ms/cm (8 times better), and the amplitude resolution is increased to about 200 uV/cm (about 5 times better). FIG. C illustrates the results produced during the AC mode wherein the filter 18 connected to the output of the high-gain amplifier 16 has been adjusted (by knob FB on the control panel) to remove the low-frequency components, thereby providing a band pass of 30–700 Hz, enabling the gain of amplifier 16 to be increased (by knob GS on the control panel) to increase its gain from 200 $\mu$V (curve B) to 10 $\mu$V (curve C), or about 100 times better than in the conventional ECG of curve A.

It will thus be seen that the illustrated apparatus permits a very substantial increase to be made both in the time base resolution and in the amplitude resolution of conventional cardiograph equipment. This increase in resolution permits the P-wave to be displayed in great detail, as shown in curves b and c of FIG. 4, so as to permit discernment of the P-wave subcomponents denoting various supraventricular structures, such as the area immediately adjacent to the S-A node, the L and R auricle, the L and R atria, and perhaps also the atrial conduction system. In addition, the HPE activity is shown as a fast deflection, superimposed on the P-wave recovery phase and the P-wave. Further, time interval measurements are more accurate; for example the P-wave begins 30 ms earlier than what would be predicted from the conventional ECG recording. In addition, the apparatus can extract the P-wave and the HPE activity from background electrical activity, and thus helps to differentiate supraventricular tachicardia (SVT) from ventricular tachicardia (VT). Still further, fine S-T segment changes (i.e., depressions or elevations) are discernable.

FIG. 5 illustrates the capability of the above-described apparatus to discern afterpotentials (AP), namely small deflections which represent abnormal slow conduction in the ventricular myocardium. This can be a very important diagnostic tool that may herald ventricular fibrillation which may be triggered by delayed conduction in a discrete region. Heretofore, afterpotentials could generally be observed only by invasive techniques by the use of a catheter introduced into the heart.

Curves A', B' and C' are actual curves produced when examining a subject generally according to the operations illustrated by curves A, B and C of FIG. 4, respectively. It will be seen that curves A' and B' show no afterpotentials, but curve C' clearly shows afterpotentials. The existence of such afterpotentials as illustrated in curve C' was verified by an invasive test performed on the subject.

While the invention has been described with respect to one preferred embodiment, it will be appreciated that many variations, modifications and applications of the invention may be made within the scope of the invention as defined in the following claims.

What is claimed is:

1. Signal processing apparatus particularly useful in electrocardiograph equipment for processing ECG signals detected by electrodes placed against the subject's body, comprising:
   (A) data amplifier means including:
      (1) a first amplifier receiving the detected ECG signals from the electrodes and producing first amplified ECG data signals according to the gain of said first amplifier, and
      (2) a second amplifier, having a substantially higher gain than said first amplifier, also receiving the detected ECG signals from the electrodes independently of said first amplifier and producing second amplified ECG data signals,
   (B) signal averaging means;
   (C) a control panel including manual selector means enabling the manual selection, for inputting into said signal averaging means and outputting to the electrocardiograph, either said first amplified ECG data signals from said first amplifier, or said second amplified ECG data signals from said second amplifier; and
   (D) a triggering circuit having a third amplifier receiving the detected ECG signals from said electrodes independently of said data amplifier means, and producing trigger pulses therefrom; and means for feeding said trigger pulses to said signal averaging means for triggering same.

2. Apparatus according to claim 1, further including a filter removing the low-frequency components of the amplified ECG data signals outputted from said second amplifier.

3. Apparatus according to claim 2, wherein said filter is a passive filter and includes means for preselecting the frequency range of the components removed from the amplified ECG data signals outputted from said second amplifier.

4. Apparatus according to claim 1, further including means enabling the outputting of said first amplified ECG data signals or of said second amplified ECG signals directly to said electrocardiograph without being processed by said averaging means.

5. Apparatus according to claim 1, wherein said control panel also includes means for manually selecting the number of ECG complexes to be used in the averaging process by said averaging means.

6. Apparatus according to claim 1, wherein said signal averaging means includes:
   a digital microcomputer;
   an analog-to-digital converter for converting the analog data from the selected amplifier to digital form before being applied to said microcomputer;
   and a digital-to-analog converter for converting the digital data from said microcomputer to analog form before being outputted to said electrocardiograph;
   said digital microcomputer being programmed to output its digital information to the digital-to-analog converter at a fraction of the speed at which it inputs its information from the analog-to-digital converter, thereby providing time-base expansion of the inputted data.

7. Apparatus according to claim 6, wherein said digital microcomputer includes storage means and said control panel includes a first manipulatible member effective, when manipulated, to start the storage in said storage means of a predetermined number of ECG complexes during the averaging process, an indicator indicating when the predetermined number of ECG complexes have been accumulated in the averaging means, and a second manipulatible member effective, when manipulated, to output the contents of the averaging means to the electrocardiograph.

8. Apparatus according to claim 1, wherein said control panel further includes means for connecting said electrodes according to one configuration when their outputs are applied to said first amplifier, or according to a different configuration when their outputs are applied to said second amplifier.

9. Apparatus according to claim 1,
   further including a display device for displaying the averaged ECG data signals outputted from the signal averaging means.

10. Apparatus according to claim 9, wherein said averaged ECG data signals are outputted from the signal averaging means in delayed time, said apparatus further including means for also applying said trigger pulses from the triggering circuit to the display device in real time without delay for also triggering said display device, thereby providing an indication, by the extent of jitter if any, of any degradation in the quality of the averaging process due to variations in time coherence between the ECG signals and the fiduciary point.

11. Apparatus according to claim 9,
   wherein said triggering circuit comprises a double-differentiator and zero-crossing detector for detecting the zero-crossing of the second derivative of the R-wave of the ECG signal from said further amplifier to produce a trigger pulse at the point of maximum slope of the R-wave.

12. Apparatus according to claim 1, further including:
   an R-wave detector receiving the amplified ECG data signals from said data amplifier means and producing an output pulse having a duration corresponding to the duration of each R-wave thereof;
   comparator means for comparing said output pulses with an average value representing the average of a plurality of said R-waves to determine whether the respective ECG complex represents an extra systole;
   and means for rejecting each ECG complex representing an extra systole from being included in said signal averaging process.

13. Apparatus according to claim 12,
   further including a signalling device and means for actuating same whenever an ECG complex representing an extra systole is located by said comparator means.

14. Apparatus according to claim 1,
   further including an RMS measuring circuit connected to the output of said data amplifier means and converting the amplified ECG data signals therefrom to RMS values; and
   a comparator comparing said RMS values with a reference level and effective to reject from the averaging process each ECG complex whose RMS level exceeds that of the reference level.

15. Apparatus according to claim 14,
   further including a manipulatible member for presetting said reference level.

16. Apparatus according to claim 1,
   further including means for measuring the effective resistance of each of the configurations of electrodes as placed against the subject's body.

17. Electrocardiograph equipment including signal processing apparatus according to claim 1,
   in combination with a plurality of electrodes adapted to be placed against the subject's body to provide ECG data signals as inputs to the signal processing apparatus, and an electrocardiograph connected to the output of said signal processing apparatus.

* * * * *